US00RE45827E

(19) United States
(12) Reissued Patent
Qian

(10) Patent Number: US RE45,827 E
(45) Date of Reissued Patent: Dec. 29, 2015

(54) SELF-SERVICE SURGICAL RETRACTOR

(71) Applicant: Jiangsu Haize Medical Scientific Development Co., Ltd., Wuxi, Jiangsu (CN)

(72) Inventor: Jianmin Qian, Jiangsu (CN)

(73) Assignee: Jianmin Qian, Shanghai (CN)

(21) Appl. No.: 14/292,724

(22) Filed: May 30, 2014

Related U.S. Patent Documents

Reissue of:
(64) Patent No.: 8,480,573
Issued: Jul. 9, 2013
Appl. No.: 13/520,085
PCT Filed: Feb. 11, 2011
PCT No.: PCT/CN2011/070922
§ 371 (c)(1),
(2) Date: Jun. 29, 2012
PCT Pub. No.: WO2012/079300
PCT Pub. Date: Jun. 21, 2012

(30) Foreign Application Priority Data

Dec. 13, 2010 (CN) ..... 2010 1 0584868

(51) Int. Cl.
*A61B 1/32* (2006.01)
*A61B 17/02* (2006.01)

(52) U.S. Cl.
CPC ..... *A61B 17/02* (2013.01)

(58) Field of Classification Search
USPC ..... 600/201, 208, 210, 217, 226, 227, 230, 600/228, 234
See application file for complete search history.

(56) References Cited

U.S. PATENT DOCUMENTS

| | | | | | |
|---|---|---|---|---|---|
| 432,614 | A * | 7/1890 | Hendrick | 600/247 |
| 3,596,946 | A * | 8/1971 | Burton et al. | 403/109.5 |
| 3,749,088 | A * | 7/1973 | Kohlmann | 600/215 |
| 4,079,978 | A * | 3/1978 | McMullin | 294/174 |
| 4,622,955 | A * | 11/1986 | Fakhrai | 600/217 |
| 4,971,038 | A * | 11/1990 | Farley | 600/230 |
| 5,897,087 | A * | 4/1999 | Farley | 248/229.21 |
| 6,090,043 | A * | 7/2000 | Austin et al. | 600/217 |
| 6,387,047 | B1 * | 5/2002 | Duhaylongsod et al. | 600/231 |
| 8,100,827 | B2 * | 1/2012 | Farley | 600/230 |
| 8,146,876 | B1 * | 4/2012 | Young et al. | 248/412 |
| 2007/0213597 | A1 * | 9/2007 | Wooster | 600/234 |
| 2009/0099421 | A1 * | 4/2009 | Shalman et al. | 600/197 |
| 2010/0145153 | A1 * | 6/2010 | Rioux et al. | 600/208 |

* cited by examiner

*Primary Examiner* — Cary Wehner
(74) *Attorney, Agent, or Firm* — Morgan, Lewis & Bockius LLP

(57) ABSTRACT

A new self-service surgical retractor with the characteristics comprising: main post (1), lock sleeve (7), lock operating lever (11), take-up device lock sleeve (15), take-up device (17) and hook plate (22). The lock sleeve (7) is covered on the lower part of the main post (1) to form a dovetail groove; the lock operating lever (11) is spun on the main post (1) through the thread; the take-up device lock sleeve (15) is spun on the upper part of the main post (1) and locks and fixes the inserted link (18) of the take-up device (17) on the upper end of the main post (1); the take-up device (17) is connected with the hook plate (22) through the retraction tape or rope (21). With simple structure and low cost, the present invention is easy to manufacture and use.

19 Claims, 4 Drawing Sheets

AMENDED

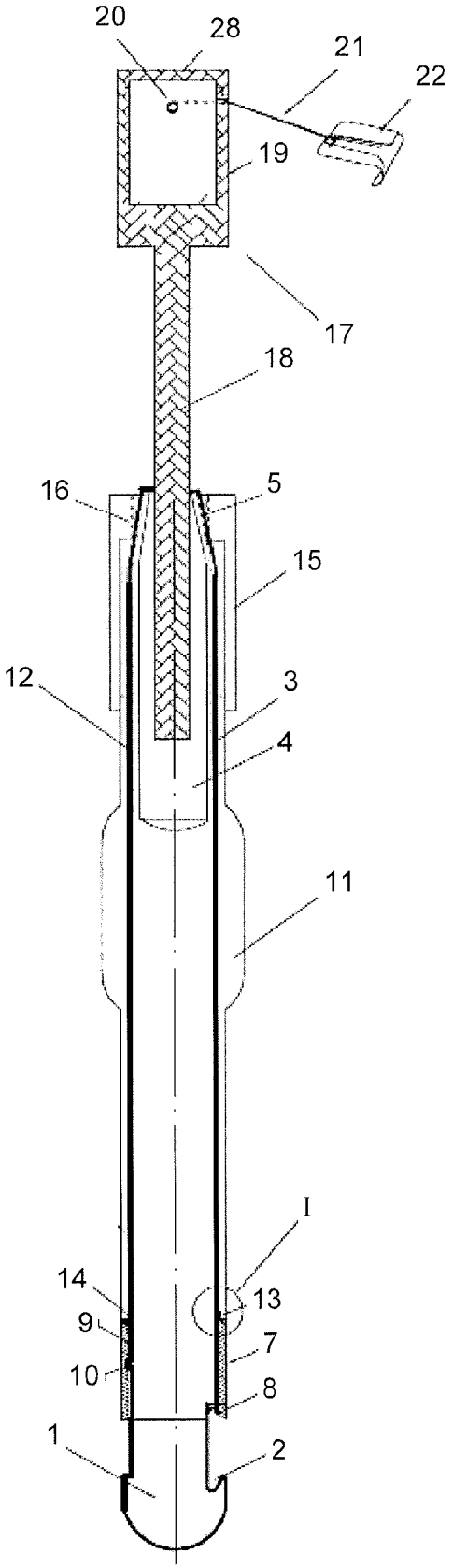
FIG. 1
AMENDED

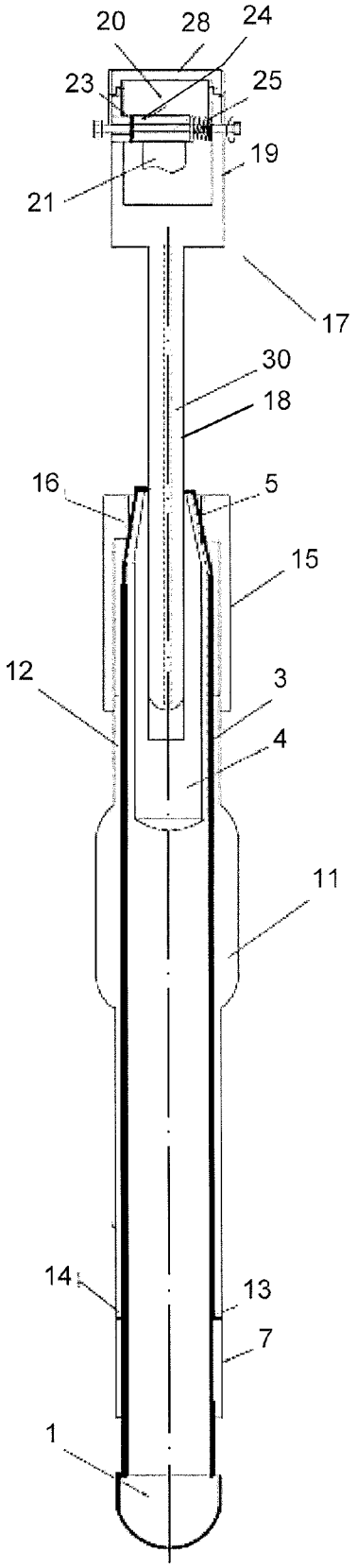
FIG. 2
AMENDED

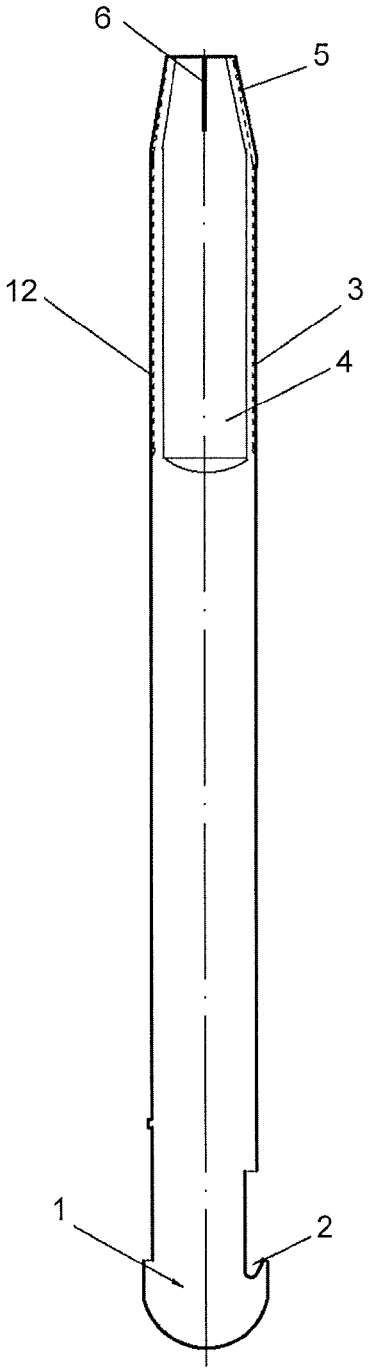
FIG. 3
AMENDED

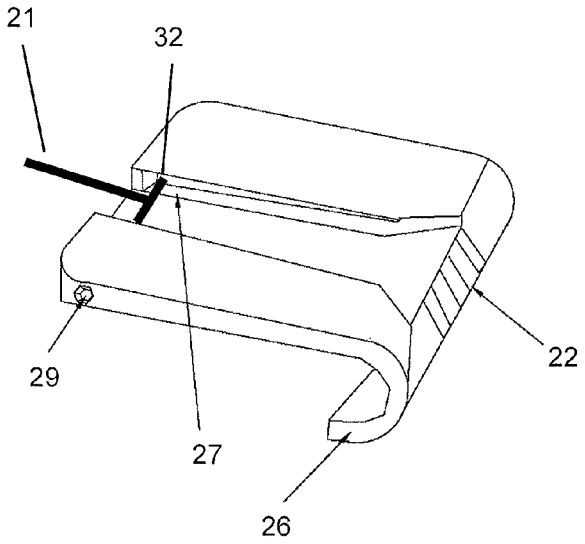
FIG. 4
AMENDED
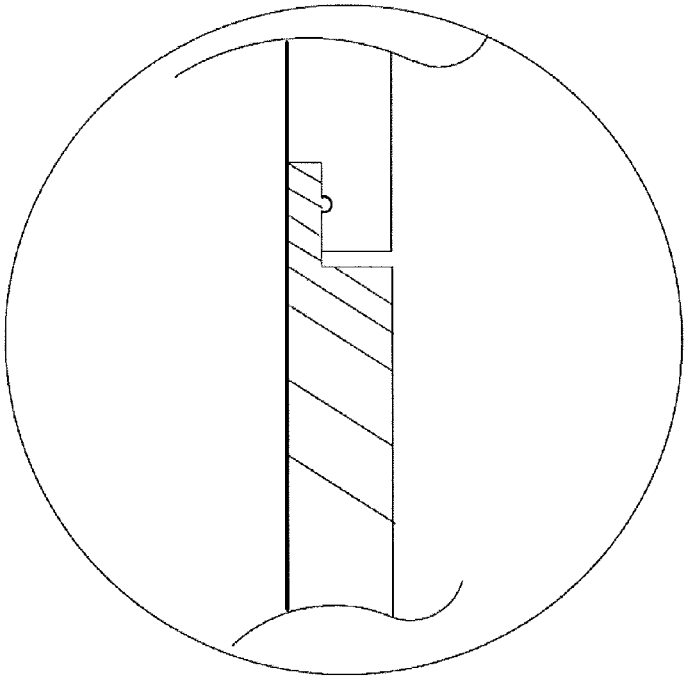
FIG. 5
AMENDED

SELF-SERVICE SURGICAL RETRACTOR

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS REFERENCE TO RELATED PATENT APPLICATION

[The present application is the US national stage of PCT/CN2011/070922 filed on Feb. 11, 2011, which claims the priority of the Chinese patent application No. 201010584868.2 filed on Dec. 13, 2010, which application is incorporated herein by reference.] *This application is a reissue application of U.S. patent application Ser. No. 13/520,085, filed on Jun. 29, 2012, which issued as U.S. Pat. No. 8,480,573 on Jul. 9, 2013, which is the US national stage of PCT/CN2011/070922 filed on Feb. 11, 2011, which claims the priority of the Chinese patent application No. 201010584868.2 filed on Dec. 13, 2010, and all of which applications are incorporated herein by reference in their entirety.*

FIELD OF THE INVENTION

The present invention relates to a medical device, especially a retractor that is used in the surgery and can retract the incision instead of manual traction in surgery, so that the surgical field can be fully exposed, specifically a new self-service surgical retractor applicable to a variety of surgeries.

BACKGROUND OF THE INVENTION

At present, the opened abdomen is required to maintain a good retraction state in order to obtain a desired surgical field during the straight abdominal incision surgery, such as general surgery, urology surgery, and obstetrics and gynecology; similarly, the incision shall also be retracted in chest, back spine and other surgeries. In one of the existing methods, the incision is opened by the surgical assistant with hooks from both sides, with poor effect and labor consumed. To this end, a variety of abdominal surgical retractors have been invented in lieu of manual traction to release people from heavy manual labor, which have made good using effects. For example, Chinese Patent No. 2006100980378, 2008101951371 and other patents are retractors specially designed for abdominal surgeries. However, during actual use, such kinds of retractors shall support multiple stayed poles connecting drag hooks on the same mounting bracket and the expansion amount of the stayed poles shall be adjusted to retract the hook plate, so the stayed poles stretch out of the surgical bed in the surgery, occupying the limited space beside the surgical bed and seriously affecting the doctors' standing position. The stayed poles stretching out of the surgical bed are also likely to cause pollution. Therefore, the positions of the existing types of retractors are constant in use to avoid the stayed poles stretching out of the surgical bed from affecting the doctors' standing position and the applicability is limited; for example, the upper abdominal retractor can only be installed above the bed head for transverse incision under the costal margin of the upper abdomen and difficult for most straight incisions and lower abdominal surgeries; while the lower abdominal retractor is very difficult to adapt to upper abdominal surgeries and even unable to adapt to the surgical retraction of other parts. Therefore, a type of convenient and effective retractors that can be moved arbitrarily beside the surgical bed as required and can retract a variety of surgical incisions without affecting the doctors' standing position with the stayed poles not stretching out of the bed when pulling the hook plate are required in clinical application. The existing various types of retractors are not qualified for above requirements. These existing retractors have a common problem, namely, large size, large quantity of parts needing on-site assembly, cumbersome use steps and high manufacturing costs, which shall be resolved. Meanwhile, the fixing devices of the existing lifting poker are also of complex structure, high manufacturing difficulty and especially inconvenient operation. In this case, the medical personnel must adjust the height with the assistance of assistants simultaneously during locking, otherwise the lifting pokers are not able to be fixed on the bedside and the height is difficult to adjust; in addition, the lifting pokers can not be easily adjusted as required during operation and will shake after being stressed due to the inconsistent width of the lock slot and bedside. To this end, the applicant has designed a patent of invention named "self-service surgical retractor" with the application number of 2010102889303, better solving the above problems. However in actual use, the applicant discovered that there are a series of problems in above patent: for example, the mobile dovetail block of the column locking mechanism shall be moved up manually and can not move up and down with the lifting poker synchronously; the take-up mechanism is more complex and the inserted link of the take-up mechanism is of large inserting resistance due to air closure.

SUMMARY OF THE INVENTION

The present invention is aimed to design a new self-service surgical retractor with simple structure, small size, simple structure of column fixed device, convenient, stable and reliable operation and applicable to the retraction of any part without affecting the doctors' standing position for the inconvenient operation and complex structure of the existing retractors.

The technical scheme of the present invention is as follows:

A new self-service surgical retractor with the characteristics including:

Main post 1, the lower end of the main post 1 is equipped with a half of dovetail groove 2 matched with the surgical bedside and the upper end is equipped with external thread 3 and a jack 4. The upper end of the said external thread 3 is of conical structure 5 and has an opening 6 along the axial direction;

Lock sleeve 7, the lock sleeve 7 is set on the main post 1. The lower end of the lock sleeve 7 is equipped with the other half of the dovetail groove 8 that can move up and down, and the said the other half of the dovetail groove 8 that can move up and down constitutes a complete dovetail groove connected with the surgical bedside with the half of dovetail groove 2; on the inner wall of the lock sleeve 7 an axial guide groove 9 is equipped, which is matched with the anti-rotation convex 10 on the lower end of the main post 1, so that the lock sleeve 7 can only move up and down along the main post 1;

Lock operating lever 11, the upper end of the lock operating lever 11 is equipped with the internal thread 12 matched with the external thread 3 on the upper end of the main post 1 and the lower end of the lock operating lever 11 is equipped with a circular groove 13, which is matched with the circular convex 14 on the upper end of the lock sleeve 7, so that the lock operating lever 11 is connected with the lock sleeve 7 and can drive the lock sleeve 7 to move up and down along the main post 1 with the lock operating lever 11;

Take-up device lock sleeve 15, the upper end of the take-up device lock sleeve 15 is equipped with the internal thread 16 matched with the external thread 3 on the upper end of the main post 1 and the lower end of the take-up device lock sleeve 15 is covered on the upper end of the lock operating lever 11;

Take-up device 17, the lower end of the take-up device 17 is equipped with an inserted link 18 that is inserted in the jack 4 on the upper end of the main post 1 and the height of the take-up device 17 can be adjusted by adjusting the position of the inserted link 18 in the jack 4; the upper end of the take-up device 17 is equipped with a take-up box 19, in which a take-up spool 20 is installed. Both ends of the take-up spool 20 stretch out of the take-up box 19, one of which acts as take-down press end and the other acts as take-up driving end; one end of the traction tape or rope 21 is fixed on the take-up spool 20 and the other end is connected with the hook plate 22 through the opening on the take-up box 19; on the said take-up box 19 the toothed sleeve 23 is fixed, the end face of the toothed sleeve is set with one-way gear; the said take-up spool 20 is also equipped with the one-way gear column 24, which is set with one-way gear on the end face, matched with the toothed sleeve 23 and can only rotate in one-way after engaged with the toothed sleeve 23; one end of the one-way gear column 24 abuts on one end of the spring 25, which always pushes the one-way gear column 24 to the toothed sleeve 23 and the other end of the spring abuts on the inner wall of the take-up box 19; the said spring 25 is cased on the take-up spool 20; the said take-up spool 20 is installed in the toothed sleeve 23;

Hook plate 22, the hook plate 22 is connected with the traction tape or rope 21 and is equipped with a hook head 26 used to hook the human tissue or abdominal wall.

The said circular convex 14 is the continuous convex ring or the convex ring composed of at least two sections of convexes.

The take-up driving end of the said take-up spool 20 is the polygon or edge circular pile structure.

One end of the said traction tape or rope 21 is connected with the one-way gear column 24 and the other end is equipped with a guide pin *32* inserted into the guide groove 27 on the hook plate 22 so as to achieve detachable connection with the hook plate 22. The width of the insert end of the guide groove 27 on the said hook plate 22 is larger than the width of the positioning end to facilitate the insertion of the guide pin *32*.

The said traction tape or rope 21 can be made of a variety of materials, such as nylon textile tape or rope, plastic braid or rope or metal flexible rope.

The said take-up box 19 is covered with an upper cover 28.

On the surface of the said inserted link 18 is opened with axial air discharge duct *30. In some embodiments, the axial air discharge duct 30 connects a closed space defined by the interior surface of the jack 3 and the exterior surface of the first end of the take-up device 17.* The said hook plate 22 is equipped with the shrinkage pool 29 matched with the take-up driving end on the take-up spool 20.

Beneficial effects of the present invention:

With simple structure and small size, the present invention is easy to operate and fits the operating habits of doctors with the space occupied only of the location of the lifting poker. The surgical incision can be effectively retracted without affecting the standing position and operation of the surgeons after the lifting poker is adjusted to the proper height.

The traction tape or rope of the present invention can be placed in the take-up box of the take-up device without occupying the space beside the surgical bed, so that the retractor can be used in any position according to actual needs without bringing any inconvenience to doctors.

The present invention can be used for the retraction of the surgical incision in any part outside the human skull, especially suitable for the retraction of the incisions with vertical angle.

Due to the use of dovetail groove structure with adjustable width in the present invention, the locking mechanism on the lower end of the lifting poker can be completely matched with the bedside and will not shake after being stressed during use, solving the stability problem in use fundamentally.

The present invention completely uses the thread structure to achieve locking and loosening, and the connection between the lower end of the lifting poker and the bedside as well as the height adjustment of the upper end can be carried out separately, so that the doctors can achieve the locking (or loosening) of the lower end and the locking (or loosening) of the stay bar only by twisting different rotation sets; in particular, the adjustment of the dovetail block opening size depends entirely on the rotation of the lock operating lever, overcoming the problem that the existing lock sleeve can only move towards one direction, that is, the narrow direction without moving up with the rotation of the lock operating lever. Therefore, the adjustment of the opening size of the dovetail groove can be achieved only with one operation, reducing the inconvenient operation of the medical personnel.

Without convex pieces, the present invention will not affect the ambulation of the medical personnel during operation, making the surgical environment clean and orderly.

The present invention adopts medical engineering plastics for injection molding to achieve mass production, so as to help reduce surgical costs as well as achieve one-time use due to low costs and reduce the occurrence of cross-infection events that may be caused by traditional reuse.

The present invention can be used for fixed surgical retractors, such as abdomen, chest and back retractors, and can be also used in other occasions in which the height of the medical devices need to be adjusted on the hospital bed.

The take-up device of the present invention adopts the principle of one-way meshing tooth with very simple structure. The take-up can be achieved only by separating the two meshing teeth, which can be reached only pressing the take-up spool during operation; once the take-up spool is released, the mutual meshing teeth will only move towards the take-up direction, so the traction tape or rope will not stretch till up to an appropriate location, ensuring the reliability of positioning. For take-up, the traction tape or rope can be withdrawn to the take-up box by only rotating the take-up spool along the rotatable direction of the one-way tooth. In addition, the present invention creatively uses the hook plate as the operating handle to operate the take-up spool and sets the operating hole on the hook plate in one end of the take-up spool stretching out of the take-up box. In this case, the traction tape or rope can be withdrawn to the take-up box by only rotating the hook plate.

BRIEF DESCRIPTION OF THE DRAWINGS

FIG. 1 is a structure diagram of the present invention.

FIG. 2 is a side elevation of FIG. 1.

FIG. 3 is a structure diagram of the main post in the present invention.

FIG. 4 is a structure diagram of the hook plate in the present invention.

FIG. 5 is a partial (I) enlarged drawing of FIG. 1.

DETAIL DESCRIPTION OF THE INVENTION

Next, let me give further explanation for the present invention based on the drawings and embodiments.

As shown in FIG. 1-4.

A new self-service surgical retractor, mainly composed of main post 1, lock sleeve 7, lock operating lever 11, take-up device lock sleeve 15, take-up device 17, traction tape or rope 21 and hook plate 22, as shown in FIG. 1 and FIG. 2. The lower end of the main post 1 is equipped with a half of dovetail groove 2 matched with the surgical bedside, and the upper end is equipped with the external thread 3 and a jack 4. The upper end of the said external thread 3 is of conical structure 5 and has an opening 6 along the axial direction, as shown in FIG. 3. The lock sleeve 7 is set on the main post 1 and connected with the lower end of the lock operating lever 11 rotatablely; the lower end of the lock sleeve 7 is equipped with the other half of the dovetail groove 8 that can move up and down, and the said the other half of the dovetail groove 8 that can move up and down constitutes a complete dovetail groove connected with the surgical bedside with the half of dovetail groove 2; on the inner wall of the lock sleeve 7 one or multiple axial guide grooves 9 is equipped, which are matched with the anti-rotation convex 10 on the lower end of the main post 1, so that the lock sleeve 7 can only move up and down along the main post 1; the anti-rotation convex 10 can be subject to injection molding with the main post 1 and also can be installed additionally with the number of one or more; the upper end of the lock operating lever 11 is equipped with the internal thread 12 matched with the external thread 3 on the upper end of the main post 1, and the upper end of the main post 1 shall stretch out of the lock operating lever 11 so as to match with the inner thread of the take-up device lock sleeve 15; the lower end of the lock operating lever 11 is equipped with a circular groove 13, which is matched with the circular convex 14 on the upper end of the lock sleeve 7 (as shown in FIG. 5), so that the lock operating lever 11 is connected with the lock sleeve 7 and can drive the lock sleeve 7 to move up and down along the main post 1 with the lock operating lever 11; the circular convex 14 can be a continuous integral structure and can also be a circular structure composed of several sections of gaps. The upper end of the take-up device lock sleeve 15 is equipped with the internal thread 16 matched with the external thread 3 on the upper end of the main post 1, and the lower end of the take-up device lock sleeve 15 is covered on the upper end of the lock operating lever 11; the upper end of the main post 1 is of conical structure 5 and has the opening 6 for tightening, so the opening on the upper end of the main post 1 shrinks when rotating the take-up device lock sleeve 15, thereby gripping the inserted link inserted in the take-up device 17 in the jack on the upper end of the main post 1 for irremovability and achieving the positioning and adjustment in the height direction. The lower end of the take-up device 17 is equipped with an inserted link 18 that is inserted in the jack 4 on the upper end of the main post 1 and the height of the take-up device 17 can be adjusted by adjusting the position of the inserted link 18 in the jack 4; on the surface of the inserted link 18 axial air discharge duct *30* is opened in order to facilitate the insertion of the inserted link 18 into the jack on the upper end of the main post 1; the upper end of the take-up device 17 is equipped with a take-up box 19, in which a take-up spool 20 is installed. Both ends of the take-up spool 20 stretch out of the take-up box 19, one of which acts as take-down press end (button sleeves that can increase the contact area for operation can be installed on the press end) and the other acts as take-up driving end (the driving end can be of polygon or edge circular pile structure matched with the socket spanner, can use the socket spanner for operation and can also directly use the hook plate of the present invention as the operating wrench simply by indicating the shrinkage pool matched with the appearance of the driving end on the hook plate); one end of the traction tape or rope 21 (nylon textile tape or rope, plastic braid or rope or metal flexible rope and the tape or rope with other types of materials can be used) is fixed on the take-up spool 20 and the other end is connected with the hook plate 22 through the opening on the take-up box 19; on the said take-up box 19 the toothed sleeve 23 is fixed, the end face of the toothed sleeve 23 is set with one-way gear; the said take-up spool 20 is also equipped with the one-way gear column 24, which is set with one-way gear on the end face, matched with the toothed sleeve 23 and can only rotate in one-way after engaged with the toothed sleeve 23; one end of the one-way gear column 24 abuts on one end of the spring 25 which always pushes the one-way gear column 24 to the toothed sleeve 23, and the other end of the spring abuts on the inner wall of the take-up box 19; the said spring 25 is cased on the take-up spool 20; the said take-up spool 20 is installed in the toothed sleeve 23; one end of the retraction tape or rope 21 is connected with the one-way gear column 24 on the take-up spool 20 and the other end is equipped with a guide pin *32* inserted into the guide groove 27 on the hook plate 22, so as to achieve detachable connection with the hook plate 22. The width of the insert end of the guide groove 27 on the said hook plate 22 is larger than the width of the positioning end to facilitate the insertion of the guide pin *32*. The hook plate 22 is connected with the traction tape or rope 21 and is equipped with a hook head 26 used to hook the human tissue or abdominal wall. Meanwhile, to play the role of wrench, the shrinkage pool 29 can be dug in suitable location of the hook plate 22 (at the location where the wall thickness is greater) instead of the socket spanner for take-up operation, as shown in FIG. 4.

Various parts of the present invention can be made of stainless steel and can also be made of medical engineering plastics. From the perspective of one-time use and cost reduction, it is better to use the medical engineering plastics with injection molding, which is not only with quality guaranteed, but also with low manufacturing cost.

The working process of the present invention is as follows:

1. Installation of Lifting Device

First rotate the lock operating lever 11 to make the opening of the dovetail groove larger than the thickness of the fixed slide rail beside the surgical bed, and then insert the dovetail groove directed at the bedside, then rotate the lock operating lever 11 and move the lock sleeve 7 down. The lock sleeve 7 can only move in axial linear direction rather than rotate with the lock operating lever 11 under the action of the anti-rotation convex 10 until the lock sleeve 7 clenches with the surgical bedside and the lock operating lever 11 can not rotate, thereby completing the locking connection with the bedside.

Then, release the take-up device lock sleeve 15; at this time, the upper end of the main post 1 is not subject to force, so that the open slot on it is stretched and the inserted link 18 can be easily drawn out from the main post 1; rotate the take-up device lock sleeve 15 again when the inserted link 18 is drawn out to the set height and then the take-up device lock sleeve 15 narrows the opening on the upper end of the main post 1 and holds tightly in the inserted link 18 and next tighten the take-up device lock sleeve 15. The removal process is just the opposite.

2. Take-Down Process:

Press the button on one end of the take-up spool 20 stretching out of the take-up box 19 and overcome the elasticity of the spring 25, and the take-up spool 20 will move so that the originally meshing one-way fluted disks are separated; since the take-up spool 20 is unconstrained at this time, just pull the retraction tape or rope 21 to pull out the belt originally wrapped around the take-up spool 20 and then release the button after pulling out to an appropriate location; the one-way fluted disks are meshed with each other at this time and are fixed at the set length since the toothed sleeve 23 is fixed on the take-up box and cannot rotate and the one-way gear column 24 on the take-up spool 20 can not cross the toothed sleeve 23 (that is, the take-up spool 20 in FIG. 2 cannot rotate counterclockwise).

3. Take-Up Process:

The retraction tape or rope can be placed in the take-up box 19 only by covering the shrinkage pool 29 which is on the socket spanner or hook plate 22 on the driving end on the take-up spool 20 to rotate the take-up spool 20 (clockwise rotation in FIG. 2).

4. Hooking of hook plate 22:

Only insert the guide pin outside the retraction tape or rope 21 in the guide groove 27 on the surface of the hook plate 22, and the guide pin *32* will not be pulled out of the hook plate 22 under the constraints of the bottom of the guide groove 27 and the gravity or tension. Simply pull the guide pin and take out the guide pin *32* reversely to take out it.

It can be seen from the embodiments that the key of the present invention is that a single surgeon can complete the assembly of the lifting device and the tightening of the retraction tape or rope without the help of assistants and the invention will not affect the activities and surgeries of doctors with the overall straight-bar structure. If required, the adjustment during the surgery can be completely accomplished by one person, thereby reducing the number of auxiliary persons in the surgery.

The part uncovered in the present invention is the same with the existing technology or can be achieved by means of the existing technology.

What is claimed is:

1. A self-service surgical retractor comprising:

[Main] *a main* post [(1)] *having an upper end and a lower end, wherein* the lower end of the main post [(1)] is equipped with a *first* half of *a* dovetail groove [(2)] matched with [the] *a* surgical bedside and the upper end *of the main post* is equipped with *an* external thread [(3)] and a jack [(4)]; [The upper end of] *and wherein* the [said] external thread [(3)] is of conical structure [(5)] and has an opening [(6)] along the axial direction;

[Lock] *a lock* sleeve [(7)] *having an upper end and a lower end, wherein:* the lock sleeve [(7)] is set on the [said] main post [(1)]; [The] *the* lower end of the lock sleeve [(7)] is equipped with [the other] *a second* half of the dovetail groove [(8)] that can move up and down [and the said], *wherein* the [other] *second* half of the dovetail groove [(8) that can move up and down], *together with the first half of the dovetail groove,* constitutes a complete dovetail groove connected with the surgical bedside [with the half of dovetail groove (2)]; *wherein,* on [the] *an* inner wall of the lock sleeve [(7)] an axial guide groove [(9)] is equipped, which is matched with [the] *an* anti-rotation convex [(10)] on the lower end of the main post [(1)], so that the lock sleeve [(7)] can only move up and down along the main post [(1)];

[Lock] *a lock* operating lever [(11)] *having an upper end and a lower end, wherein* the upper end of the lock operating lever [(11)] is equipped with [the] *an* internal thread [(12)] matched with the external thread [(3)] on the upper end of the main post [(1)] and the lower end of the lock operating lever [(11)] is equipped with a circular groove [(13)], which is matched with [the] *a* circular convex [(14)] on the upper end of the lock sleeve [(7)], so that the lock operating lever [(11)] is connected with the lock sleeve [(7)] and can drive the lock sleeve [(7)] to move up and down along the main post [(1)] with the lock operating lever [(11)];

[Take-up] *a take-up* device lock sleeve [(15)] *having an upper end and a lower end, wherein* the upper end of the take-up device lock sleeve [(15)] is equipped with the internal thread [(16)] matched with the external thread [(3)] on the upper end of the main post [(1)] and the lower end of the take-up device lock sleeve [(15)] is covered on the upper end of the lock operating lever [(11)];

*a hook plate, wherein the hook plate is connected with traction tape or rope and is equipped with a hook head used to hook human tissue or an abdominal wall; and*

[Take-up] *a take-up* device [(17)] *having an upper end and a lower end, wherein* the lower end of the take-up device [(17)] is equipped with an inserted link [(18)] that is inserted in the jack [(4)] on the upper end of the main post [(1)] and the height of the take-up device [(17)] can be adjusted by adjusting the position of the inserted link [(18)] in the jack [(4)]; the upper end of the take-up device [(17)] is equipped with a take-up box [(19)], in which a take-up spool [(20)] is installed; [Both] *both* ends of the take-up spool [(20)] stretch out of the take-up box [(19)], one of which acts as *a* take-down press end and the other acts as *a* take-up driving end; one end of the traction tape or rope [(21)] is fixed on the take-up spool [(20)] and the other end is connected with the hook plate [(22)] through [the] *an* opening on the take-up box [(19)]; on the [said] take-up box [(19) the] *a* toothed sleeve [(23)] is fixed, the end face of the toothed sleeve is set with *a* one-way gear; the [said] take-up spool [(20)] is also equipped [with] *a* the one-way gear column [(24)], which is set with *the* one-way gear on the end face matched with the toothed sleeve [(23)] and can only rotate in one-way after engaged with the toothed sleeve [(23)]; one end of the one-way gear column [(24)] abuts on one end of [the] *a* spring [(25)] which always pushes the one-way gear column [(24)] to the toothed sleeve [(23)] and the other end of the spring abuts on the inner wall of the take-up box [(19)]; the [said] spring [(25)] is cased on the take-up spool [(20)]; the said take-up spool [(20)] is installed in the toothed sleeve [(23); Hook plate (22), the hook plate (22) is connected with the traction tape or rope (21) and is equipped with a hook head (26) used to hook the human tissue or abdominal wall].

2. The self-service surgical retractor of claim 1, [the characteristic of the said new self-service surgical retractor is that the said] *wherein the* circular convex [(14)] is [the] *a* continuous convex ring or [the] *a* convex ring composed of at least two sections of convexes.

3. The self-service surgical retractor of claim 2, [the characteristic of the said new self-service surgical retractor is that] *wherein* the take-up driving end of the [said] take-up spool [(20)] is [the] *a* polygon [or edge circular pile structure].

[4. The self-service surgical retractor of claim 1, the characteristic of the said new self-service surgical retractor is that one end of the said traction tape or rope (21) is connected with the one-way gear column (24) on the take-up spool (25), and the other end is equipped with a guide pin inserted into the guide groove (27) on the hook plate (22) so as to achieve detachable connection with the hook plate (22); The width of the insert end of the guide groove (27) on the said hook plate (22) is larger than the width of the positioning end to facilitate the insertion of the guide pin.]

5. The self-service surgical retractor of claim 1, [the characteristic of the said new self-service surgical retractor is that the said] *wherein the* traction tape or rope [(21) can be] *is* made of nylon textile tape or rope, plastic braid or rope or metal flexible rope.

6. The self-service surgical retractor of claim 1, [the characteristic of the said new self-service surgical retractor is that the said] *wherein the* take-up box [(19)] is covered with an upper cover [(28)].

7. The self-service surgical retractor of claim 1, [the characteristic of the said new self-service surgical retractor is that on] *wherein* the surface of the [said] inserted link [(18)] is opened with *an* axial air discharge duct.

8. The self-service surgical retractor of claim 1, [the characteristic of the said new self-service surgical retractor is that the said] *wherein the* hook plate [(22)] is equipped with [the shrinkage pool (29)] *an indentation* matched with the take-up driving end on the take-up spool [(20)].

*9. A self-service surgical retractor comprising:*

*a main post having a first end and an opposite second end, wherein the main post is equipped with a mounting mechanism near the first end to mount the main post to a surgical bed and a supporting mechanism near the second end;*

*a take-up device having a first end and an opposite second end, wherein the first end of the take-up device is configured to rotatably engage the supporting mechanism near the second end of the main post such that the take-up device is configured to move in both first and second directions along an axis of the main post;*

*a take-up device lock sleeve, wherein the take-up device lock sleeve is configured to lock the take-up device onto the main post when the take-up device lock sleeve moves in the first direction along the axis of the main post and release the take-up device from the main post when the take-up device lock sleeve moves in the second direction along the axis of the main post;*

*a take-up box mounted near the second end of the take-up device, wherein the take-up box is equipped with a retractable mechanism and a lock mechanism for locking/unlocking the retractable mechanism; and*

*a hook plate that is connected to the retractable mechanism, wherein the hook plate is equipped with a hook head used to hook the human tissue or abdominal wall.*

*10. The self-service surgical retractor of claim 9, wherein the mounting mechanism of the main post is equipped with an adjustable dovetail groove for engaging a sidebar of the surgical bed.*

*11. The self-service surgical retractor of claim 10, wherein the mounting mechanism of the main post further includes a lock sleeve for forming a half of the adjustable dovetail groove.*

*12. The self-service surgical retractor of claim 11, wherein the lock sleeve is configured to engage the main post via an anti-rotation convex and a lock operating lever via a circular convex, respectively, such that a rotation movement of the lock operating lever along the axis of the main post results in a translation movement of the lock sleeve along the axis of the main post so as to adjust the width of the adjustable dovetail groove.*

*13. The self-service surgical retractor of claim 9, wherein the supporting mechanism of the main post is equipped with a jack at the second end for hosting the first end of the take-up device and an external thread near the second end for engaging the take-up device lock sleeve.*

*14. The self-service surgical retractor of claim 13, wherein the take-up device lock sleeve is equipped with an internal thread for engaging the external thread near the second end of the main post such that a clockwise rotation movement of the take-up device lock sleeve along the axis of the main post presses an interior surface of the jack against an exterior surface of the first end of the take-up device and a counter-clockwise rotation movement of the take-up device lock sleeve along the axis of the main post releases the interior surface of the jack from the exterior surface of the first end of the take-up device.*

*15. The self-service surgical retractor of claim 14, wherein the take-up device is equipped with an axial air discharge duct connecting a closed space defined by the interior surface of the jack and the exterior surface of the first end of the take-up device.*

*16. The self-service surgical retractor of claim 15, wherein the retractable mechanism of the take-up box is equipped with a spring wrapping around the axis of the take-up spool with one end fixed onto the take-up spool and another end fixed onto the take-up box to draw the hook plate closer to the take-up box.*

*17. The self-service surgical retractor of claim 16, wherein the lock mechanism includes a toothed sleeve mounted on the take-up box, the toothed sleeve including a one-way gear surface facing a one-way gear column mounted near a first end of the take-up spool, and a pressure by the spring causes the one-way gear column to engage the one-way gear surface into a locked state and a counter-pressure against the spring's pressure causes the one-way gear column to disengage the one-way gear surface such that the hook plate can be pulled away from the take-up box.*

*18. The self-service surgical retractor of claim 17, wherein the take-up box is equipped with a tightening mechanism for rotating the one-way gear column and the spring around the axis of the take-up spool while the one-way gear column is engaged with the toothed sleeve by the spring's pressure.*

*19. The self-service surgical retractor of claim 9, wherein the retractable mechanism of the take-up box is equipped with a take-up spool and a traction rope wraps around an axis of the take-up spool with one end fixed onto the take-up spool and another end connected to the hook plate through an opening on the take-up box.*

*20. The self-service surgical retractor of claim 19, wherein the traction rope is equipped with a guide pin that is detachably inserted into a guide groove on the hook plate.*

* * * * *